United States Patent [19]

Wilwerding

[11] Patent Number: 4,931,167

[45] Date of Patent: Jun. 5, 1990

[54] DEGRADATION OF POLYCHLORINATED BIPHENYLS

[75] Inventor: Carl M. Wilwerding, Klamath Falls, Oreg.

[73] Assignee: Advanced Refinery Technology, Klamath Falls, Oreg.

[21] Appl. No.: 341,316

[22] Filed: Apr. 21, 1989

Related U.S. Application Data

[63] Continuation of Ser. No. 108,190, Oct. 13, 1987, abandoned.

[51] Int. Cl.[5] .......................... C10G 17/00; C07C 1/30

[52] U.S. Cl. ................................. 208/262.5; 210/909; 423/659; 423/DIG. 20; 585/469

[58] Field of Search .......................... 208/262.1, 262.5; 423/659, DIG. 20; 210/906, 909; 585/469

[56] References Cited

U.S. PATENT DOCUMENTS

| | | | |
|---|---|---|---|
| 4,053,401 | 10/1977 | Fukushima et al. | 210/914 |
| 4,351,978 | 9/1982 | Hatano et al. | 585/469 |
| 4,410,422 | 10/1983 | Brunelle | 208/262 |
| 4,469,661 | 9/1984 | Schultz | 423/210.5 |
| 4,547,620 | 10/1985 | Miyata et al. | 208/262 |
| 4,623,448 | 11/1986 | O'Connell et al. | 208/262 |
| 4,639,309 | 1/1987 | Lalancettle et al. | 585/469 |
| 4,659,443 | 4/1987 | Byker | 204/190 |
| 4,663,027 | 5/1987 | Mendiratta et al. | 208/262.1 |
| 4,681,045 | 7/1987 | Duirka et al. | 423/232 |
| 4,721,824 | 1/1988 | McWilliams | 208/262 |

FOREIGN PATENT DOCUMENTS

| | | | |
|---|---|---|---|
| 52-57149 | 5/1977 | Japan | 423/659 |

*Primary Examiner*—Gary P. Straub

*Attorney, Agent, or Firm*—Townsend and Townsend

[57] ABSTRACT

Polychlorinated biphenyls are chemically degraded by contact with a Lewis acid catalyst in a non-aqueous liquid medium, in the presence of a cation which combines with the chlorines on the PCBs to form a solid chloride of the cation which will precipitate out from the liquid medium. Preferred Lewis acids are metal halides, particularly a combination of aluminum chloride and ferric chloride, and the preferred cation is potassium in the form of potassium hydroxide. The process is susceptible to both batch and continuous operation.

31 Claims, 2 Drawing Sheets

DEGRADATION OF POLYCHLORINATED BIPHENYLS

This is a Continuation of application, Ser. No. 07/108,190 filed October 13, 1987 now abandoned.

BACKGROUND OF THE INVENTION

This invention relates to the disposal of polychlorinated biphenyls, commonly known as PCBs.

In their most common form, PCBs are mixtures of isomers of trichlorobiphenyl, tetrachlorobiphenyl, pentachlorobiphenyl, and small amounts of dichlorobiphenyl and hexachlorobiphenyl. Up until the early 1970's PCBs were used in a wide range of applications due to their unique blend of fire resistance, thermal and oxidative stability, electrical characteristics, solvency, inertness and liquid range. Some of their most important uses were as follows: as a dielectric medium in transformers, either alone or in blends with other materials such as trichlorobenzene; as the dielectric impregnating medium in capacitors; as plasticizers; as ingredients in lacquers, paints and varnishes and adhesives; as water proofing compounds in various types of coatings; as lubricants or lubricant additives under extreme conditions; as heat transfer fluids; as fire resistant hydraulic fluids; as vacuum pump fluids; and as air compressor lubricants. Their largest application was in the electrical industry as a dielectric medium in transformers and capacitors.

In the late '60's and early '70's, it was discovered that PCBs have a major potential for enironmental contamination due to their extremely slow biodegradation rates. The persistance and toxicity of PCBs have prompted governmental action restricting their use and application, and the Toxic Substances Control Act of 1976 contained provisions for discontinuance of their use and for their eventual disposal. Even trace amounts of PCBs are considered undesirable.

Current regulations issued by the Evironmental Protection Agency Specify incineration as the only acceptable method of PCB disposal in the absence of special clearance. Incineration, of course, expensive and hazardous, and in cases where the PCBs are a minor component mixed in with a nonprohibited fluid such as one of the various types of replacement dielectric fluids, one loses the nonprohibited fluid as well by incinerating the entire mixture.

SUMMARY OF THE INVENTION

It has now been discovered that PCBs are chemically degraded upon contact with a Lewis acid catalyst. The degradation is performed in the presence of a cation which combines with the chloride ion liberated by the degradation of the PCBs to form a solid precipitate which can readily be removed. The process can be performed on PCBs in solution in a wide range of concentrations, including trace amounts, permitting full recovery of the bulk of the solution free of PCBs. The process may be incorperated in a batch, continuous, or semi-continuous process. Further features, advantages and embodiments of the invention will be evident from the description which follows.

DETAILED DESCRIPTION OF THE INVENTION AND PREFERRED EMBODIMENTS

Figure 1:
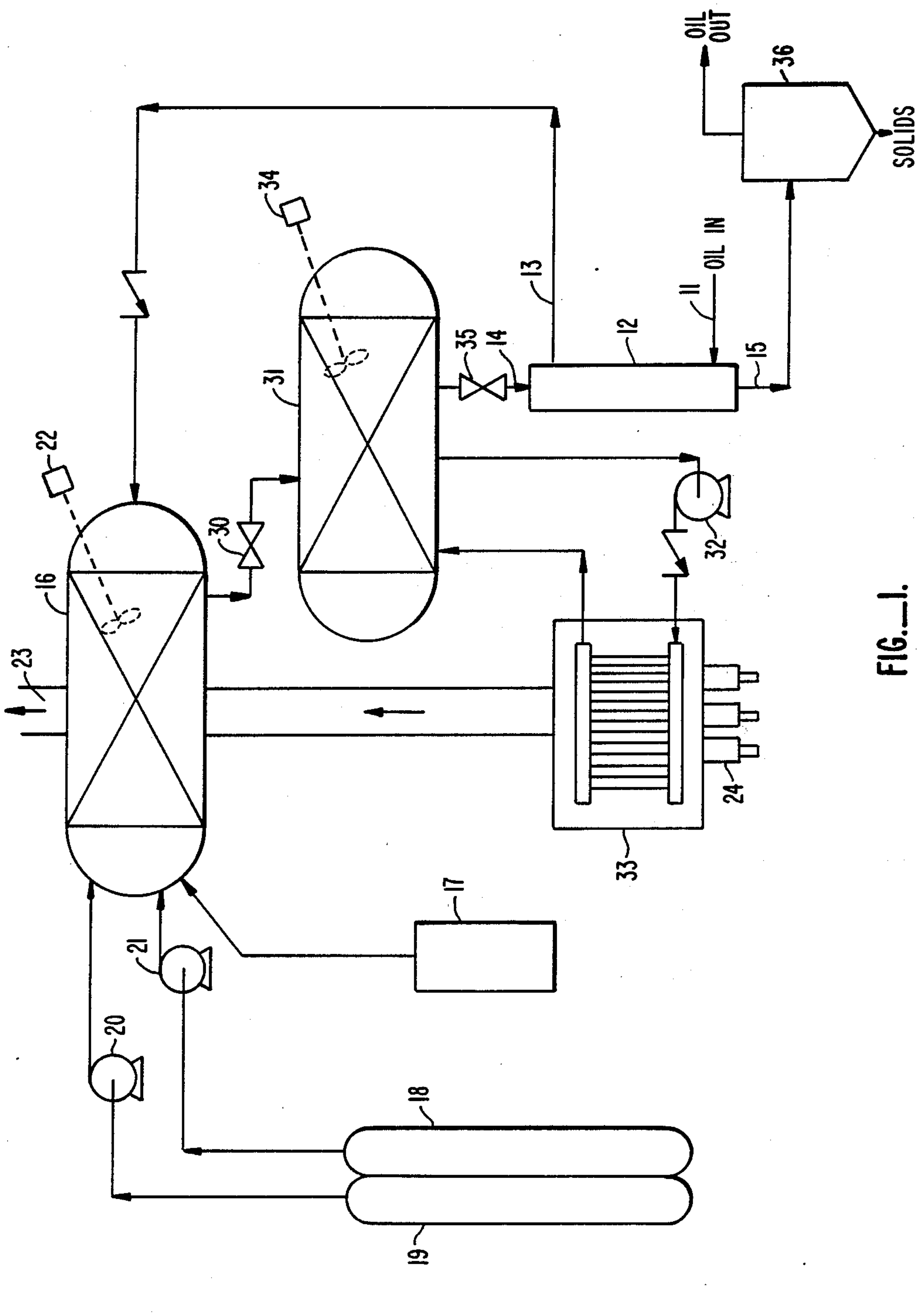
FIG. 1 is a flow diagram for a batchwise process in accordance with one embodiment of the present invention.

The term "Lewis acid " is used herein in accordance with its commonly accepted meaning in the chemical field i.e., a molecule or ion which combines with a second molecule or ion by forming a covalent bond with two electrons from the latter. Preferred Lewis acids are metal halide-type Lewis acids, which have an electron-deficient central metal atom capable of electron acceptance. Among these, halides of aluminum, beryllium, cadmium, zinc, boron, gallium, titanium, zirconium, tin, antimony, bismuth, iron and uranium are preferred. The preferred halides are chlorides and bromides. Combinations of species are also included within the scope of the invention. Particularly preferred Lewis acids are aluminum and ferric halides, particularly aluminum and ferric chlorides ($AlCl_3$ and $FeCl_3$). In the most preferred embodiments of the invention, aluminum chloride and ferric chloride are used in combination. The Lewis acid must be used in anhydrous form.

The cation which combines with the liberated chloride ion to form a precipitate is preferably an alkali or alkaline earth metal ion. Particularly preferred metal ions are sodium, potassium and calcium, potassium being the preferred. The cation may be added to the reaction medium in any form which will render it available for reaction with the chloride ion. The metal hydroxide is a particularly preferred form.

The process is applicable to PCBs present as contaminants in nonaqueous fluids, in concentrations as low as 10 ppm, preferably from about 100 to about 10,000 ppm. The process of the invention requires a substantially anhydrous reaction medium. If water is present in the contaminated fluid, substantially removed first, for example by vacuum dehydration. If the fluid which is contaminated by the PCBs is water itself, the PCBs cab be extracted with toluene to form a toluene solution of the PCBs. The toluene solution is then treated in accordance with the present invention.

Nonaqueous solvents which are miscible with the liquid medium containing the PCBs can be used to dissolve the Lewis acid catalyst and cation to facilitate their addition to the contaminated liquid. Low boiling solvents are preferred in view of the ease in which they can be evaporated from the reaction mixture prior to bringing the mixture up to reaction temperature. Particularly preferred solvents are alcohols, with methanol being a particularly convenient choice. The use of anhydrous aluminum chloride, ferric chloride dissolved in methanol, and potassium hydroxide dissolved in methanol, both of the latter in the highest concentration achievable, are particularly effective. As one example of the proportions which may be used, based on a 1000-gallon (3785-liter) quantity of contaminated oil containing 500 ppm PCBs, one may use 6 lbs (2.4 kg) of anhydrous $AlCl_3$, 1 gallon (3.785 liters) of a solution of 60% $FeCl_3$ dissolved in methanol, and 1.5 gallons (5.7 liters) of a solution of approximately 25% potassium hydroxide in methanol.

The ratios may be varied widely, and are not critical. In general, however, best results will be achieved with a weight ratio of Lewis acid to PCBs ranging from about 0.5:1 to about 50:1, preferably from about 1:1 to about 20:1. When aluminum chloride and ferric chloride are used, the preferred ranges are from about 1:1 to about 10:1 for each. The cation which combines with the liberated chloride ion is generally used in excess. When the source of the cation is potassium hydroxide, best results are achieved when the latter is used to a weight ratio of from about 1:1 to about 20:1 with respect to the PCBs.

The reaction is conducted at elevated temperature, although the temperature itself is not critical and can vary widely. An appropriate temperature range will be high enough to provide a reaction rate which will achieve completion of the reaction within a reasonable, economically efficient period of time, yet not so high as to break down the Lewis acids or convert the desirable components of the contaminated medium in which the PCBs are contained. With these considerations in mind, reaction temperature will generally be at least about 100° C. For most systems, temperatures within the range of about 100° C. to about 500° C., preferably from about 300° C. to about 350° C., will provide the best results. The pressure may also vary widely. Atomspheric pressure is sufficient for most applications.

The reaction may be performed in either batchwise, continuous, or semi-continuous manner. In a batch process or the batch portion of a semi-continuous process, the reaction time will vary depending on the reaction conditions, the concentration of PCBs, and the ratios of system components. The appropriate length of time can be readily determined in each case by one skilled in the art using routine monitoring techniques, such as periodic sampling and analysis by chromatography. In general, at temperatures above 300° C., trace amounts of PCBs (on the order of 1000 ppm) will be completely degraded within about 2 hours.

Once the reaction is complete, any solids precipitating as a result of the reaction, particularly the chloride salts, are readily removed by conventional techniques such as, for example, filtration, decantation, and centrifugation.

As one example of a continuous process, the contaminated liquid medium to be treated may be passed through a bed of solid particles containing the Lewis acid and a solid form of the cation. The particles may consist of crystallized forms of the Lewis acid and a compound of the cation. In th alternative, the solid particles may consist of inert solid carrier materials supporting the active species, either by impregnation or surface coating. The bed may be a fixed or fluidized bed.

The Lewis acid and cation particles may be mixed together or separated into individual layers so that the contaminated liquid passes through them in sequence. In the latter case, it is preferred that the Lewis acid be contacted first, followed by the cation. When the Lewis acid is a combination of aluminum chloride and ferric chloride, it is further preferred that the aluminum chloride be the first layer contacted, followed by the ferric chloride. With layered beds, still better results are achieved using repeated sets of layers for the contaminated liquid to be passed through in succession. The contaminated liquid may also be continuously circulated through the mixed or layered bed for further reaction. The proportions of the various system components and the conditions of temperature and pressure described inconnection with the batch process are applicable here as well.

A semi-continuous process arrangement may, for example, use alternating circulation loops in timed sequence. Such arrangements will be readily apparent to those skilled in the art.

Turning now to the figures, FIG. 1 is a process flow diagram for a batch process version of the present invention.

Contaminated oil enters at an oil output 11 to a heat exchanger 12, which it leaves through an oil exit line 13. In the heat exchanger 12, this feed oil is contacted with and heated by hot oil emerging from the reaction zone. The latter (decontaminated) oil enters by a product oil inlet 14 and leaves by a product oil outlet 15 after having been cooled by the feed oil to a temperature of approximately 100° C. The feed oil is simultaneously heated to about 90° C.

The heated feed oil is then fed to a mixing vessel 16, where it is combined with anhydrous aluminum chloride supplied from a holding vessel 17, ferric chloride in methanol solution from a holding vessel 18, and potassium hydroxide in methanol solution from a holding vessel 19. The latter two, being in liquid form, are fed to the mixing vessel 16 through a dual pump 20, 21. The components are stirred in the mixing vessel 16 by a motorized agitator 22, and the temperature is raised by heat from the exhaust gases 23 from a series of burners 24 in a heating chamber used in a downstream section of the process. The reaction mixture is retained in the mixing vessel 16 until a temperature of approximately 250° C. is reached. For a 1000-gallon batch of contaminated oil, using approximately 1–2 gallons each of the two liquid additives and 5–10 lbs of the solid aluminum chloride, a residence time in the mixing vessel of about one-half hour will be sufficient.

Once the reaction mixture has reached the desired temperature in the mixing vessel 16, an exit valve 30 is opened, permitting passage of the reaction mixture into a reaction vessel 31. The reaction mixture is circulated from this reaction vessel 31 by way of a circulation pump 32 through a shell-and-tube heat exchanger 33, fired by the aforementioned burners 24, to slowly raise the temperature of the reaction mixture to the desired reaction temperature, typically approximately 322° C. A motorized agitator 34 continuously stirs the reaction mixture as it circulates to avoid uneven or excessive heating. The reaction mixture is retained in the reaction vessel 31 at the reaction temperature until the reaction is complete, typically about 1 to 2 hours for a 1000-gallon batch.

Once the reaction is complete, an exit valve 35 is opened, permitting the reaction mixture to pass through the aforementioned heat exchanger 12, to be cooled down while heating the incoming feed oil. The cooled reaction mixture is then passed to a separator 36, in which the salts settle out and the oil is removed by decantation. The spent salts include the potassium chloride precipitated as a result of the degradation of the PCBs and may be flushed with water and discarded.

Figure 2:
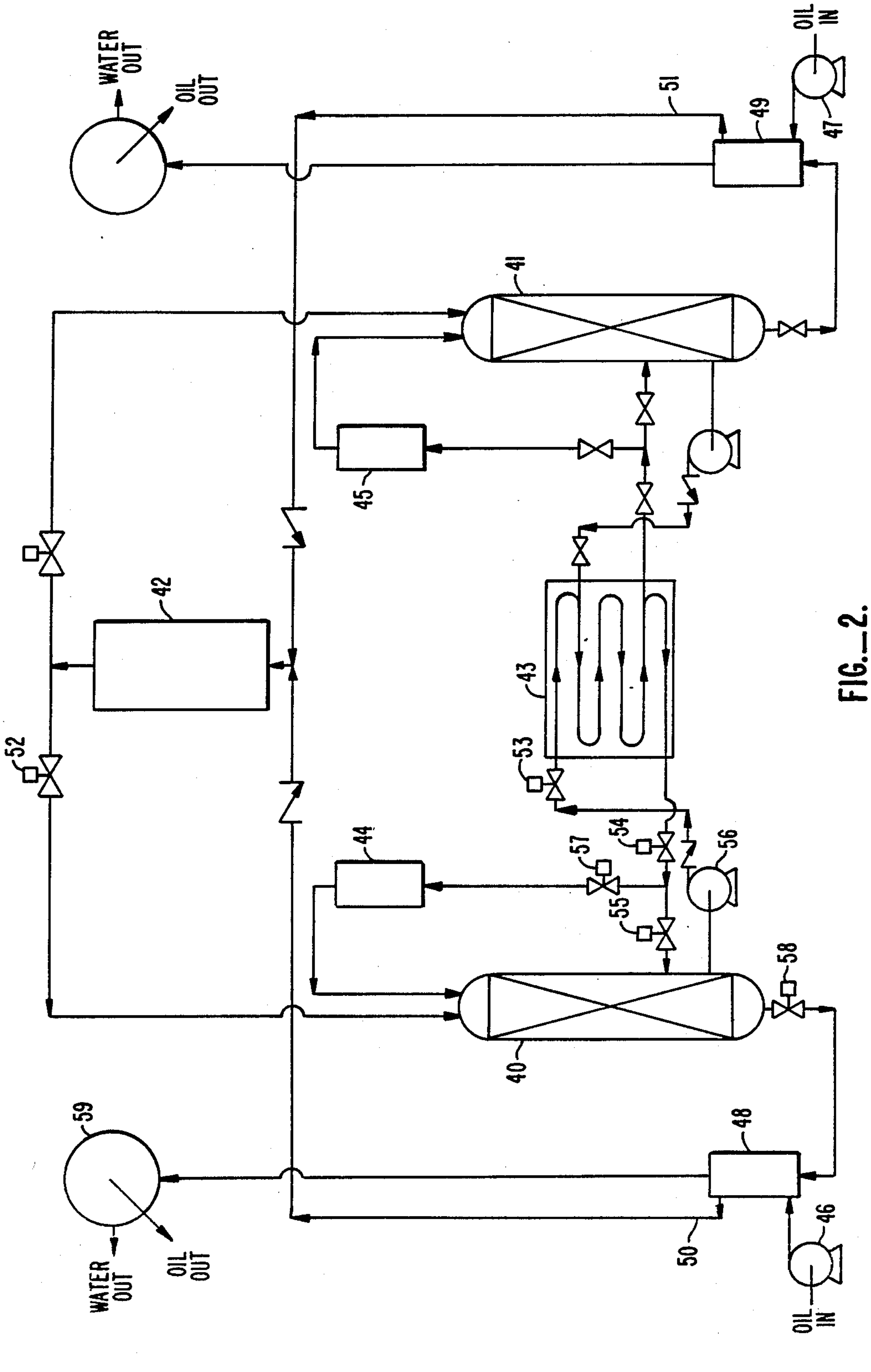
FIG. 2 is a flow diagram for a continuous process in accordance with a second embodiment of the present invention.

FIG. 2 depicts a process flow diagram for a semi-continuous or continuous-batch process. This system has two reaction vessels 40, 41 for alternating use, utilizing a common preheat tank 42, with the contents of each reaction vessel further heated by circulation through a common heat exchanger 43. All three tanks are equipped with air relief valves. The Lewis acid and cation components of the system are used in this process in the form of beds of solid particles which the reaction mixture passes through. Two such beds 44, 45 are included, one for each of two reaction vessels 41, 41.

To begin a typical running sequence, the preheat tank 42 is filled with contaminated oil by either of two gear pumps 46, 47. To do this, these pumps direct the feed oil first to one of two heat exchangers 48, 49 which permits heat exchange with decontaminated product mixture in the same manner as the entering heat exchanger 12 of the batch process of FIG. 1. The heated oil emerges from the heat exchanger through an oil outlet line 50, 51 which feeds the oil to the preheat tank 42. This tank also serves as a storage tank for retaining a batch of contaminated oil while a previous batch is being treated.

The running sequence for reaction tank 40 may then be started by filling the reaction tank 40 with oil from the preheat tank 42 through valve 52, then opening valves 53, 54 and 55, and actuating a gear pump 56 which draws the reaction vessel contents out of the reaction vessel and circulates it through the heat exchanger 43. This circulation is continued until the desired temperature is reached. Valve 55 is then closed and valve 57 is opened, directing the contaminated oil through the catalyst bed 44. The reaction mixture thus circulates through both the heat exchanger 43 and the catalyst bed 44 for a sufficient period of time to achieve complete conversion of the PCBs.

The configuration of the catalyst bed, as indicated above, may assume any of a variety of forms. As one example, sequenced layers of aluminum chloride, ferric chloride, and potassium hydroxide in the form 16-mesh granules may be used, in layers one-half inch (1.3 cm) in depth, supported by 350-mesh stainless steel screens, leaving room for fluidization, typically one-quarter inch (0.64 cm) clearance above each layer. Several groups of these layers, such as for example, 10 groups, may be used for further efficiency. Circulation through the catalyst bed may be continued until the reaction is complete. As before, this is readily determined by routine monitoring. For a 1000-gallon batch, a typical circulation time will be 0.75 hour.

After the passage of a preselected period of time, the valves 55 and 57 are closed, the gear pump 56 is turned off, and the drain valve 58 is opened. This permits passage of the treated oil through the initial heat exchanger 48, where its temperature is lowered to approximately 100° C. Upon leaving this heat exchanger, the cooled oil is fed to a separator 59, which functions in the same manner as the separator 36 of the batch process of FIG. 1, including the use of water to rinse the potassium chloride before the latter is discarded. In a preferred use of this embodiment, valves 52, 53, 54 and 58 are electrically controlled valves and valves 55 and 57 are thermally controlled.

The corresponding valves and gear pump in association with the second reaction vessel 41 are then energized in the same sequence. This can be done during draining of the first reaction vessel simultaneously with the heating of feed oil through the initial heat exchanger 48 and in the preheat tank 42.

The following example is offered for purposes of illustration, and is intended neither to define nor limit the invention in any manner.

EXAMPLE

A reaction vessel was charged with 300 ml by weight of transformer oil, Univolt N-61, obtained from Exxon, St. Paul, Minnesota, spiked with approximately 500 ppm of Aroclor 1260, a polychlorinated biphenyl obtained from National Electric, St. Paul, Minnesota 5 grams $AlCl_3$, 1.5 grams $FeCl_3$, and 0.5 gram of a 25% solution of KOH in methanol.

The mixture was gradually heated and agitated until the methanol has been evaporated. The mixture was then brought to a temperature of 325° C. and held at this temperature for 1.5–2 hours. Samples were drawn periodically and analyzed by chromatography. At the end of the time period indicated above, the chromatogram showed a complete absence of PCBs.

It was noted during the reaction that no distillates other than the methanol were collected. The lighter hydrocarbons in the transformer oil merely refluxed. PCB analysis was done by ASTM method D-4059, using packed column gas chromatography and an electron capture detector, yielding a final result of less than 1 ppm PCBs.

The foregoing is offered primarily for purposes of illustration. It will be readily apparent to those skilled in the art that the various elements of the process as well as materials and equipment described for use herein in connection with the invention may be further varied, modified or substituted without departing from the spirit and scope of the invention.

What is claimed is:

1. A process for degrading polychlorinated biphenyls in a nonaqueous liquid medium, said process comprising contacting said medium under anhydrous conditions with a metal halide Lewis acid in the presence of a metal hydroxide in alcohol solution, the metal of which metal hydroxide combines with chlorine to form a solid precipitate in said nonaqueous medium at an elevated temperature, to precipitate at least a substantial portion of the chlorine in said polychlorinated biphenyls as the chloride salt of said cation.

2. A process in accordance with claim 1 in which said metal halide is a member selected from the group consisting of metal chlorides, metal bromides and combinations thereof.

3. A process in accordance with claim 1 in which said metal halide is a member selected from the group consisting of aluminum, beryllium, cadmium, zinc, boron, gallium, titanium, zirconium, tin, antimony, bismuth, iron and uranium halides and combinations thereof.

4. A process in accordance with claim 1 in which said metal halide is a member selected from the group consisting of aluminum and ferric halides and combinations thereof.

5. A process in accordance with claim 1 in which said metal halide is a member selected from the group consisting of aluminum and ferric chlorides and combinations thereof.

6. A process in accordance with claim 1 in which said metal halide is a combination of aluminum chloride and ferric chloride.

7. A process in accordance with claim 1 in which said metal hydroxide is selected from the group consisting of alkali and alkaline earth metal hydroxides.

8. A process in accordance with claim 1 in which said metal hydroxide is selected from the group consisting of sodium, potassium and calcium hydroxides.

9. A process in accordance with claim 1 in which said metal hydroxide is potassium hydroxide.

10. A process in accordance with claim 1 in which said elevated temperature is at least about 100° C.

11. A process in accordance with claim 1 in which said elevated temperature is from about 100° C. to about 500° C.

12. A process in accordance with claim 1 in which said elevated temperature is from about 300° C. to about 350° C.

13. A process in accordance with claim 1 in which said process is conducted in batchwise manner.

14. A process in accordance with claim 13 in which the weight ratio of said Lewis acid to said polychlorinated biphenyls is from about 0.5:1 to about 50:1.

15. A process in accordance with claim 13 in which the weight ratio of said Lewis acid to said polychlorinated biphenyls is from about 1:1 to about 20:1.

16. A process in accordance with claim 13 in which said metal hydroxide is present in sufficient quantity to precipitate substantially all of the chlorine in said polychlorinated biphenyls.

17. A process in accordance with claim 13 in which said Lewis acid is comprised of a combination of aluminum chloride and ferric chloride, each at a weight ratio of from about 1:1 to about 10:1 with respect to said polychlorinated biphenyls, and said metal hydroxide is potassium hydroxide at a weight ratio of from about 1:1 to about 20:1 with respect to said polychlorinated biphenyls.

18. A process in accordance with claim further comprising removing said precipitated chloride salt from said nonaqueous liquid medium.

19. A process for degrading polychlorinated biphenyls in a nonaqueous liquid medium, said process comprising contacting said medium under substantially anhydrous conditions with aluminum chloride and ferric chloride in the presence of potassium hydroxide in alcohol solution at an elevated temperature to precipitate at least a substantial portion of the chloride in said polychlorinated biphenyls as potassium chloride.

20. A process for degrading polychlorinated biphenyls in a nonaqueous liquid solution thereof, said process comprising:

(a) combining said solution under substantially anhydrous conditions with solid anhydrous aluminum chloride in a weight ratio ranging from about 1:1 to about 10:1 with respect to said polychlorinated biphenyls, ferric chloride in alcohol solution in a weight ratio ranging from about 1:1 to about 10:1 ferric chloride to polychlorinated biphenyls, and potassium hydroxide in alcohol solution at a weight ratio of from about 1:1 to about 20:1 potassium hydroxide to polychlorinated biphenyls, to form a substantially homogeneous reaction mixture;

(b) evaporating substantially all alcohol from said reaction mixture;

(c) heating said reaction mixture to a temperature ranging from about 300° C. to about 350° C. to degrade a substantial portion of said polychlorinated biphenyls and precipitate the chlorine therein as potassium chloride; and (d) removing substantially all solids from said reaction mixture.

21. A process for degrading polychlorinated biphenyls in a nonaqueous liquid medium, said process comprising passing said nonaqueous liquid medium through a bed of solid particles containing a metal halide Lewis acid and a metal hydroxide, the metal of which hydroxide combines with chlorine to form a solid precipitate in said nonaqueous medium.

22. A process in accordance with claim 21 in which said Lewis acid and said metal hydroxide are separated into individual layers in said bed.

23. A process in accordance with claim 21 in which said Lewis acid is a member selected from the group consisting of metal chlorides, metal bromides and combinations thereof and said metal hydroxide is selected from the group consisting of sodium, potassium and calcium hydroxides.

24. A process in accordance with claim 21 in which said Lewis acid is a member selected from the group consisting of aluminum and ferric halides and combinations thereof and said compound of said metal hydroxide is selected from the group consisting of sodium, potassium and calcium hydroxides.

25. A process in accordance with claim 21 in which said metal halide is a combination of aluminum chloride and ferric chloride and said metal hydroxide is potassium hydroxide.

26. A process in accordance with claim 21 comprising passing said nonaqueous liquid medium through a bed of solid particles, said bed divided into a first layer comprising aluminum chloride, a second layer comprising ferric chloride, and a third layer comprising potassium hydroxide.

27. A process in accordance with claim 26 comprising passing said nonaqueous liquid medium through said first layer first, said second layer second and said third layer third.

28. A process in accordance with claim 26 in which said first, second and third layers are defined as a set, and said bed comprises a plurality of said sets in succession arranged in sequence.

29. A process for degrading polychlorinated biphenyls in a nonaqueous liquid medium, said process comprising passing nonaqueous liquid medium through a bed of solid particles, said bed divided into a first layer comprising aluminum chloride, a second layer comprising ferric chloride, and a third layer comprising potassium hydroxide, at a temperature of at least about 100° C.

30. A process in accordance with claim 29 in which said temperature is from about 100° C. to about 500° C.

31. A process in accordance with claim 29 in which said temperature is from about 300° C. to about 350° C.

* * * * *